United States Patent [19]
Filippi et al.

[11] Patent Number: 4,875,031
[45] Date of Patent: Oct. 17, 1989

[54] VAPOR MONITORING SYSTEM
[76] Inventors: Ernest A. Filippi, P.O. Box 1809, Porterville, Calif. 93258; Kenneth L. Miller, 22209 Halldale Ave., Torrance, Calif. 90501
[21] Appl. No.: 134,866
[22] Filed: Dec. 18, 1987
[51] Int. Cl.⁴ .............................................. G01B 21/00
[52] U.S. Cl. ........................................ 340/605; 73/23
[58] Field of Search ................ 340/605; 73/23, 40.5 R
[56] References Cited
U.S. PATENT DOCUMENTS

| | | | |
|---|---|---|---|
| 3,924,442 | 12/1975 | Kerho et al. | 73/23 X |
| 4,166,380 | 9/1979 | Batz | 73/23 |
| 4,644,333 | 2/1987 | Barendsz et al. | 73/23 X |
| 4,646,069 | 2/1987 | Andrejasich et al. | 340/605 X |
| 4,665,385 | 5/1987 | Henderson | 73/23 X |
| 4,736,193 | 4/1988 | Slocum et al. | 340/605 X |

Primary Examiner—Stewart J. Levy
Assistant Examiner—Joseph W. Roskos

[57] ABSTRACT

A hazardous gases detector that is completely self contained and small enough to fit into small diameter pipe bores. The system is housed in two sealed enclosures, one housing the detection circuits and batteries and the other the signal output. The two components are connected by a length of electrical cable. The invention detects BTX vapors in monitor well bores or piping connected to the detection volume of dual walled underground fuel storage tanks. The signal output end of the invention caps the well or conduit and suspends the sensor end in the well bore or conduit. The detection circuit and battery end is suspended ten feet or more below the gound level and thusly ensures uniform temperature, and thus stable performance of the detector. Circuits that time vapors sampling interval provide long term operation from a battery comprised of six standard "D" size cells, leak detection is signaled by blinding lights and horn, with two weeks of signal capacity in the battery, a minimum. Internal non-reversible indication of leak detection is also provided. The lower housing is intrinsic safe by pressure containment and the upper housing by current limitation. The system can be varied to function from a solar cell battery combination and transmit signals by radio. Installation does not require electrical or signal wiring, thus is not susceptable to technician error for installation and service.

19 Claims, 9 Drawing Sheets

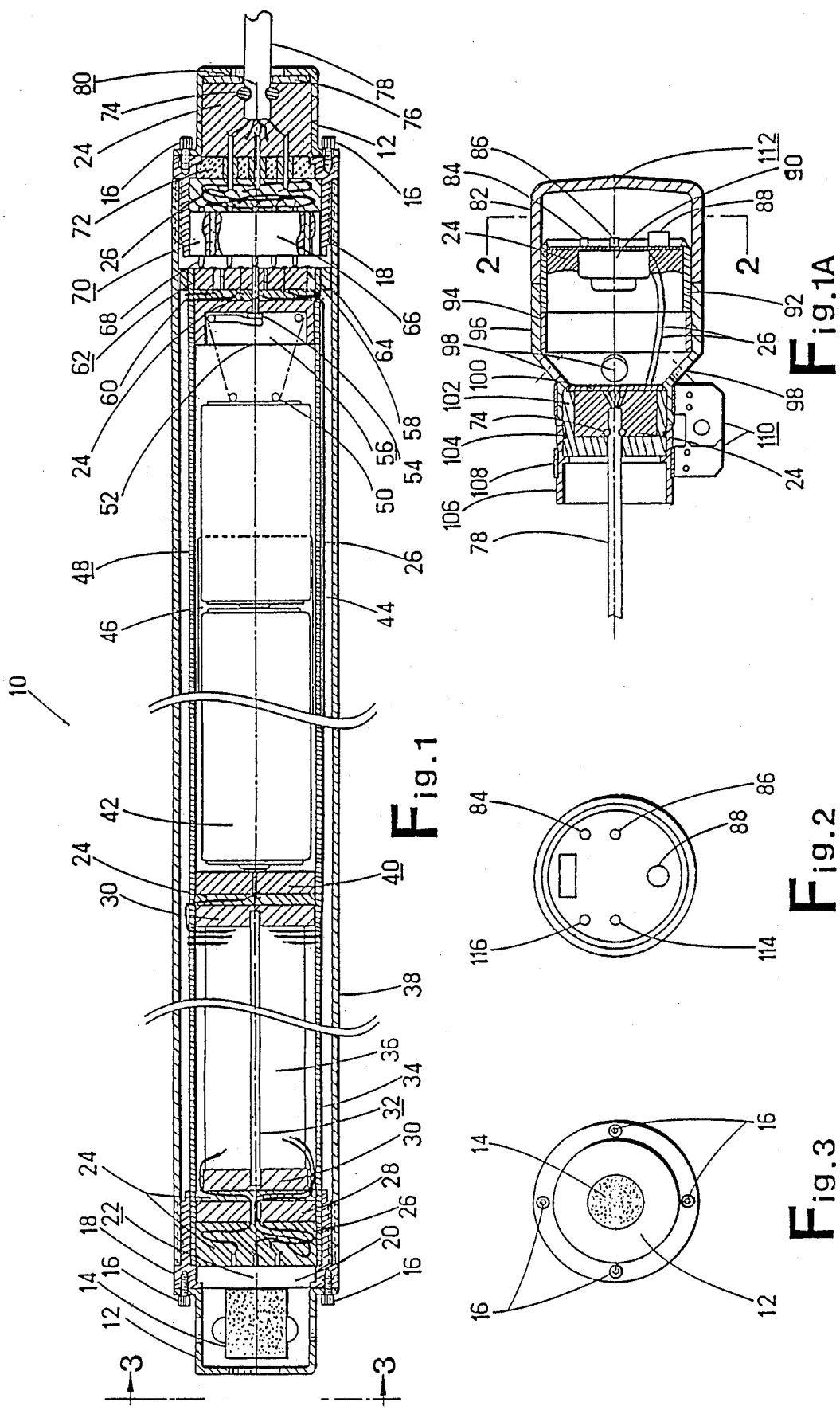

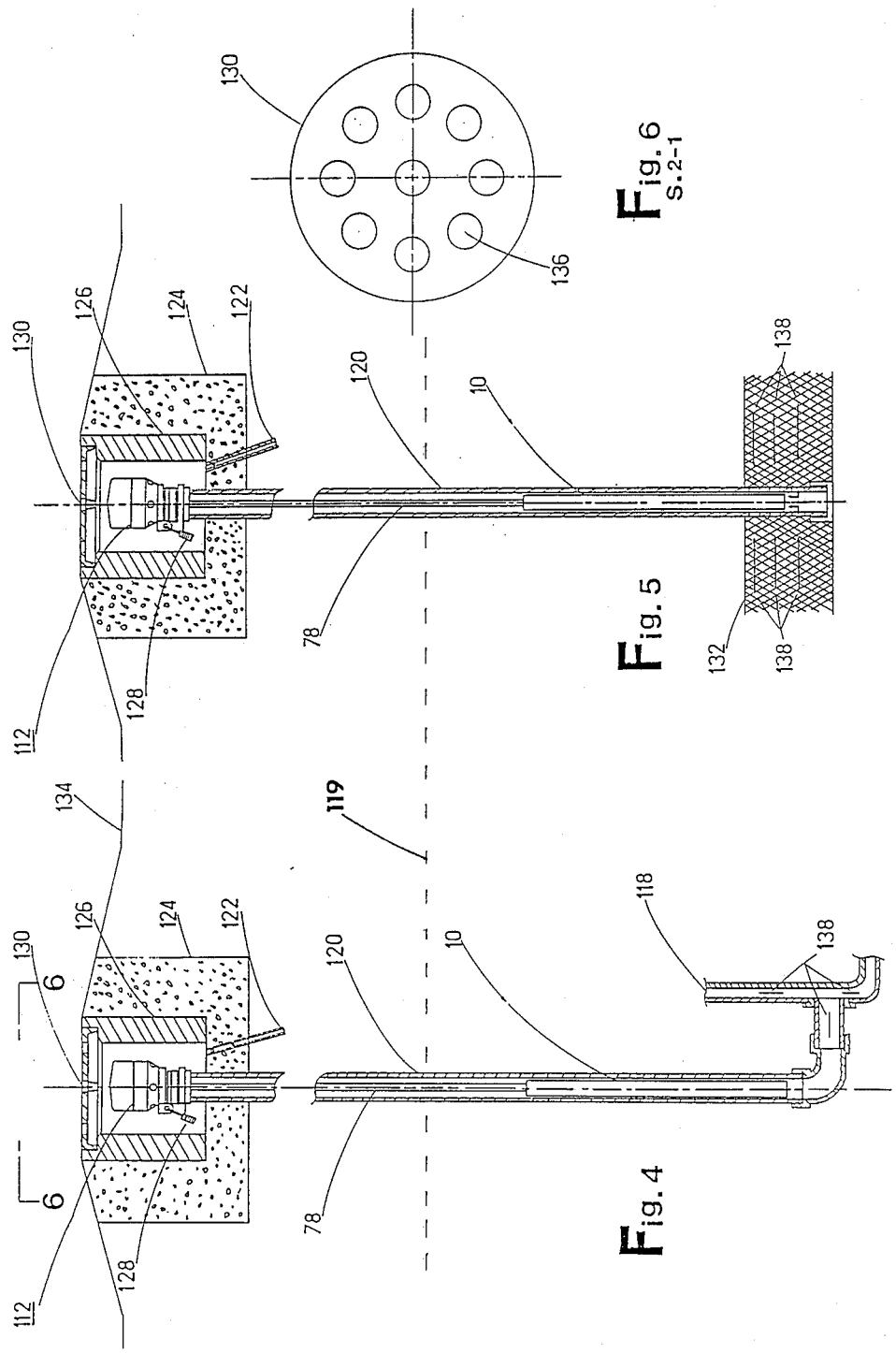

RADIO FREQUENCY COMMUNICATION

TELEPHONE MODEM COMMUNICATION

VAPOR MONITORING SYSTEM

BACKGROUND OF THE INVENTION

1. Field of the Invention

This invention relates to the detection of the presence of Benzene, Toluene and Xylene (BTX) in surface and ground waters and adjacent soils. The absence of said hydrocarbons relating to underground fuel storage tanks must be demonstrated by requirement of Federal and State law, by the operators of said tanks.

2. Description of Prior Art

Heretofore the absence or presence of BTX in surface and ground waters and adjacent soils was demonstrated by leak testing of adjacent underground fuel storage tanks. This leak determination method employed filling the tank being tested with fuel and measuring the fuel subsidence, as measured by viewing the fuel level change in a graduated glass column, over a time interval. Variance due to fluid temperature change and air entrapment is compensated for by computation and operator skill.

Leak determination of underground fuel storage tanks is also achieved by inventory reconciliation methods. In such methods the operator balances the volume of fuel in, versus the volume of fuel out and cmpares ending inventories with starting inventories. A computer variant of the above checks storage tank fuel level for subsidence during closed hours, while correcting for temperature changes in the fuel. Fuel lines from submersible pumps to dispensers, are checked for leakage, by a valve arrangement that terminates fuel flow if expected fuel line pressure is not achieved.

Drilling test holes adjacent to underground fuel storage tanks and sampling the adjacent soil and water for the BTX components of fuel is used in some situations. A variance of the above, is to case the sample hole with casing at the top and perforations at the bottom of the casing and monitor for BTX vapors.

New installations utilize double wall underground tanks and double wall flow lines to contain any leak. Instrumentation sensing BTX vapors signal a leak in the inner wall of the tank. Also loss of vacuum in the volume between the underground tanks inner and outer walls is used to indicate a leak, in some designs.

A disclosed leak detection method also describes a grid of low voltage wires that change resistance when exposed to BTX fluid and the resistance change is used to signal a leak.

Determination of tank leakage by observation of the subsidence of fuel in a glass column has been proven by EPA tests to have a larger error factor than the leak rate to be determined. Additionally this test is usually performed only annually and any leak that developed immediately thereafter would be undetected for nearly a year. In this probable scenario the tank operator would face a very large clean-up expense.

Determination of leakage by inventory reconciliation faces the same problem of accuracy of measurement. Usually fluid level is determined by manually sticking the tank with a wooden stick graduated in inches, subdivided to quarter of inches. Any settling of the tank from level or operator inconsistencies will affect accuracy. Although computerizing the above test method and using, fuel height, fuel level and temperature sensors does improve probably accuracy, small leaks may not be detected.

Drilling the annually test holes and sampling surface and ground waters and soils for BTX, cannot be disputed for accuracy. Economy precludes performing these tests more than annually, therefore, this method suffers because it does not detect a leak that occurs in the interval between tests.

Improving the method above involves drilling permanent monitor wells and placing BTX vapor sensors in the vadose zone adjacent to the underground tanks to be monitored. The reliability of vapor detection for leak determination of BTX fluids is clearly shown in the study conducted by Campo/Miller and presented in the report entitled : "Test report for evaluation of BTX (Naptha) migration patterns through various soils when discharged from leaking underground storage tanks", published by Campo/Miller.

Currently several manufacturers offer instrumentation for sale that places a sensor in the monitor well bore, said sensor is connected by wiring to electronics that perform the test for BTX vapors. Usual installation involves drilling and completing monitor wells, and placing at remote locations electronics connected by buried wiring to a sensor in the monitor well bore. The cost of tearing up concrete and asphalt paving to lay the signal line has prohibited this approach from broad use, particularly in existing tank installations. New installations with double wall tanks are not as greatly affected by cost increases due to having to run signal lines from the down hole sensor, in this case the sensor conduit is vented to the volume between the tanks inner and outer walls. However, having to run underground signal lines can be a cost deterent to use in large pipe line and tank farm installations.

In its optimum form a completely self contained BTX vapor sensor, intrinsically safe, with the ability to signal the presence of BTX vapors in a monitor well or a double wall storage tank would have great advantages over the current state-of-art. Such a device would fit into a two inch or smaller diameter pipe and signal leakage by visual, audible, radio or telephonic means. The scope of the invention presented herein delineates such a device.

OBJECTS OF THE INVENTION

Accordingly, it is an object of the present invention to provide an improved system for detection of leaks from underground fuel storage tanks.

It is another object of the present invention to provide a BTX vapor detection system not requiring wiring to an outside power source.

It is another object of the presented invention to provide a BTX vapor detection system not requiring wiring to an outside communication source.

It is another object of the presented invention to provide a BTX vapor detection system small in size that will function in small diameter conduit pipe.

It is another object of the presented invention to provide a BTX vapor detection system that will function in small diameter monitor wells without requiring outside wiring for power or communication.

It is another object of the presented invention to provide a BTX vapor detection system that will function in small diameter conduit pipe, connected to the leak detection chamber of a dual wall underground fuel storage tank, without requiring outside wiring for power or communication.

It is another object of the presented invention to provide a BTX vapor detection system that is an integrated assembly, that will function in hot and cold weather extremes and when batteries are used; replacement shall not be required sooner than twelve months.

It is another object of the presented invention to provide a BTX vapor detection system that incorporates intrinsically safe features as defined by Underwriters Laboratories for explosive environments.

It is another object of the presented invention to provide a BTX vapor detection system suitable for fuel transmission pipeline leak detection, the system being compatible in certain configurations with solar cell plus battery power source and radio communications.

It is another object of the presented invention to provide a BTX vapor detection system suitable for fuel leak detection in a plurality of applications.

It is another object of the presented invention to provide a vapors detection system suitable for detection of a plurality of vapors, with minor circuit modification.

It is another object of the presented invention to provide a vapors detection system that is low cost, reliable and easy to use.

Further objects and advantages of our invention will become apparent from a consideration of the drawings and the ensuing description.

DRAWING FIGURES DESCRIPTION

FIGS. 1 & 1A Show a longitudinal section view of preferred embodiment of present invention.

FIG. 2 Shows a top view of the instrument cap assembly with a protective cover removed.

FIG. 3 Shows a bottom view of the instrument body assembly delineating the end of the housed catalytic sensor component.

FIG. 4 Shows one application of use of the preferred embodiment.

FIG. 5 Shows one application of use of the preferred embodiment.

FIG. 6 Shows special modification of street box cover.

Figure 7:
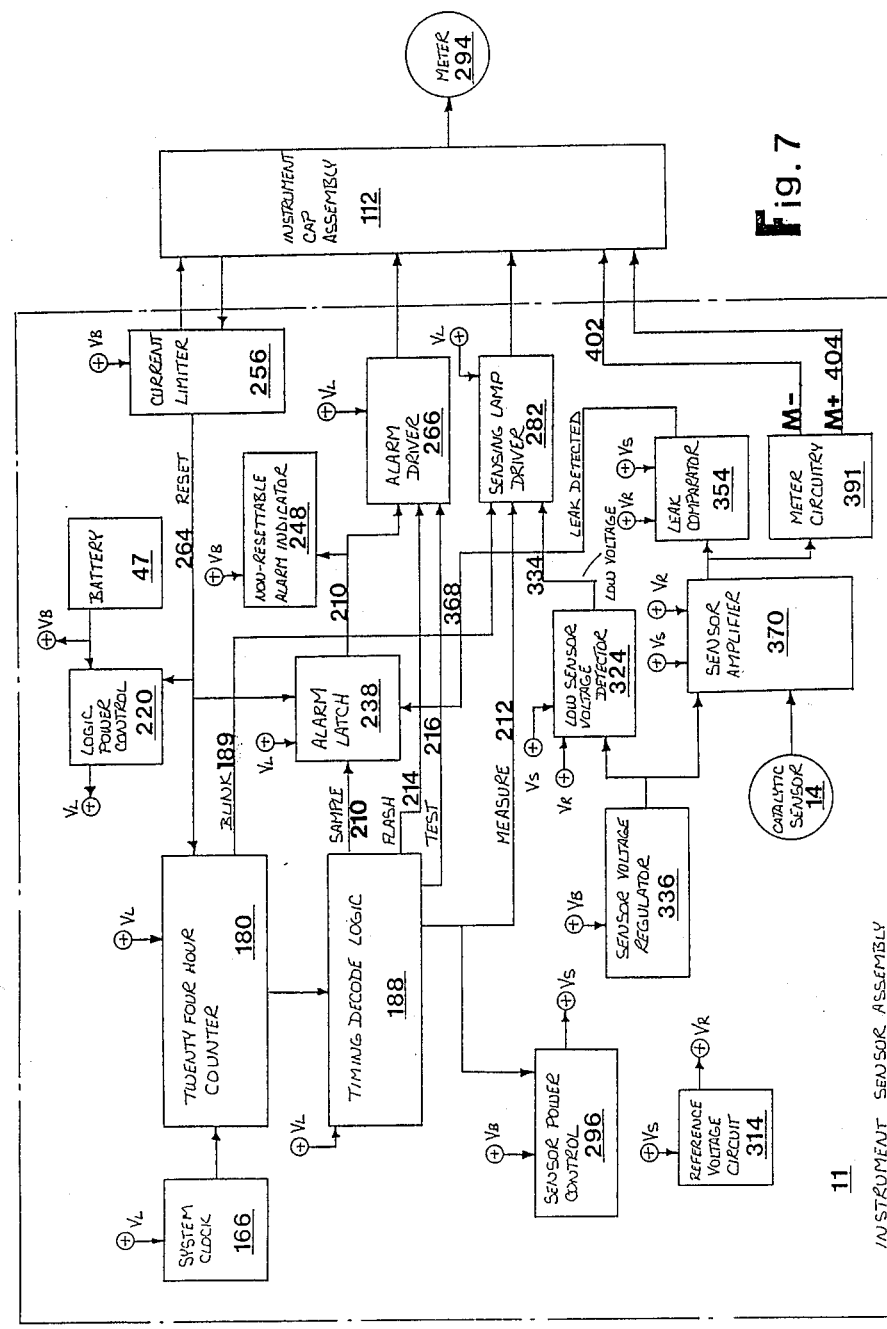

FIG. 7 Block diagram for preferred embodiment vapor monitoring electronics.

Figure 8:
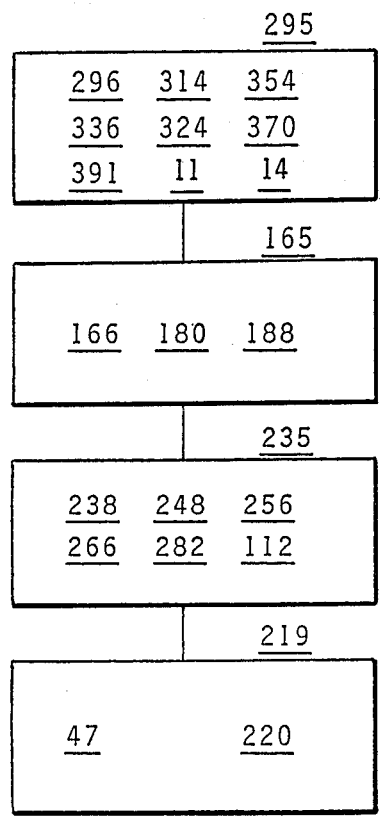

FIG. 8 Block diagram for sensing, timing, signalling and power elements of preferred embodiment.

Figure 8A:
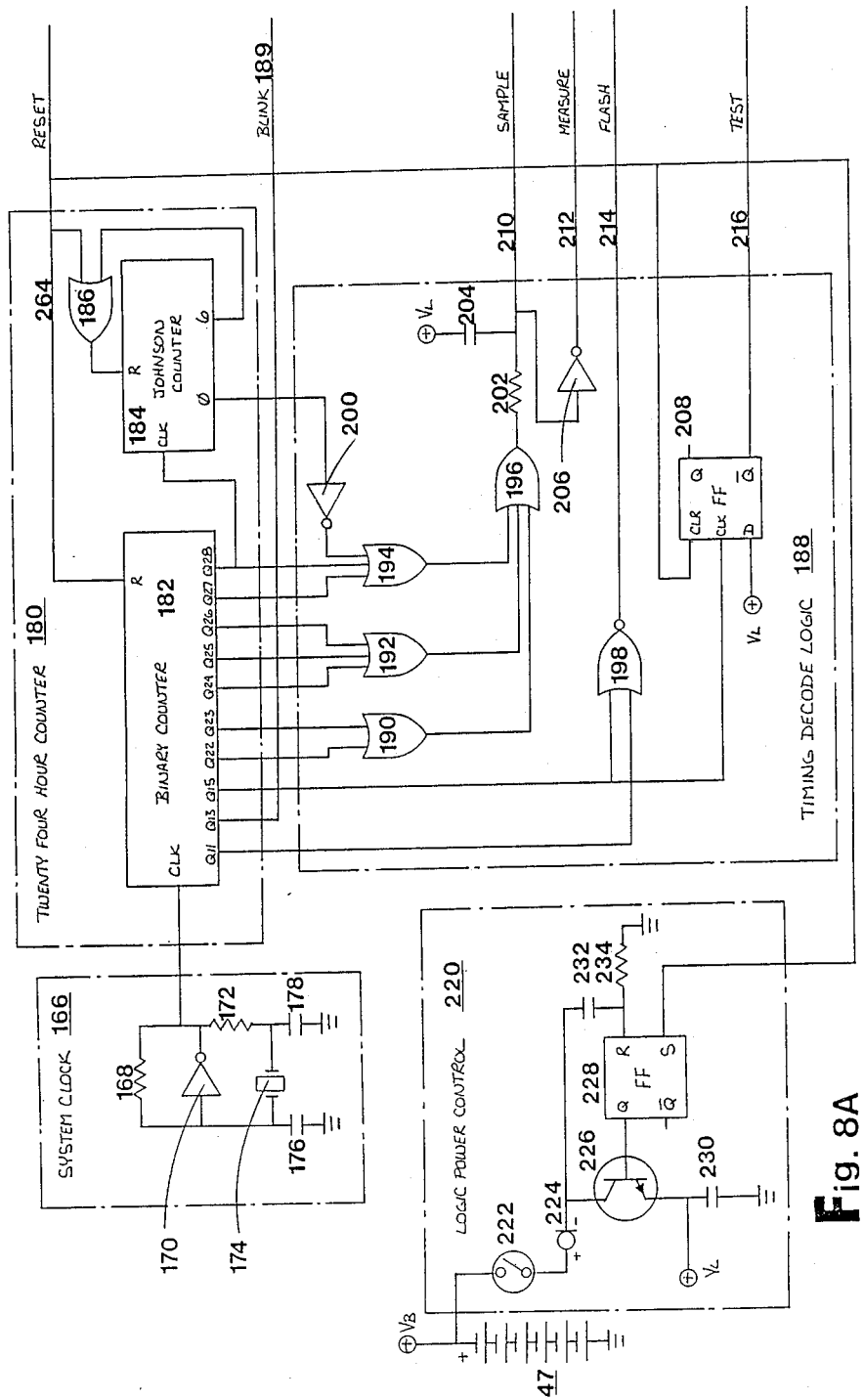

FIG. 8A Schematic diagram for power and timing elements.

Figure 8B:
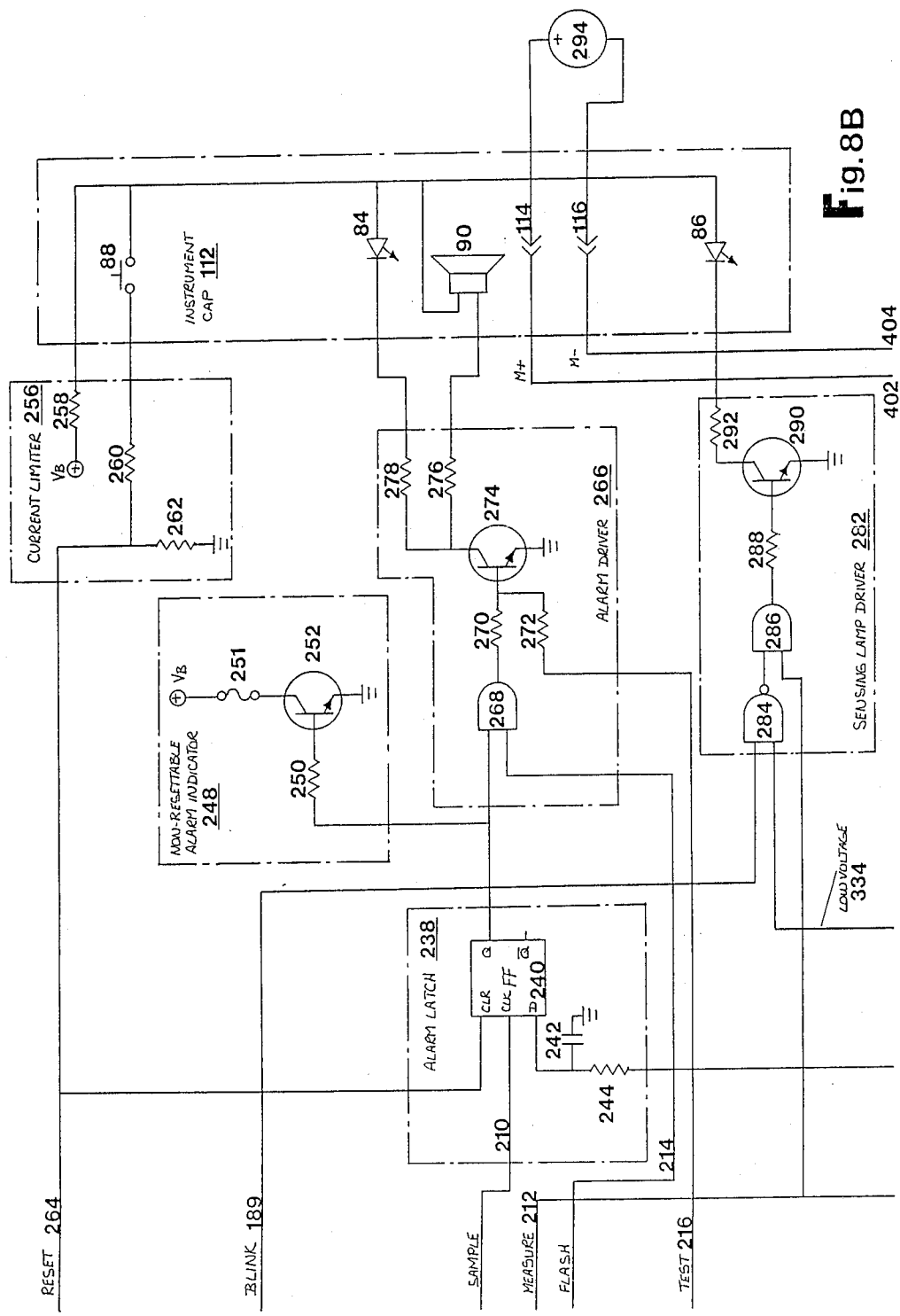

FIG. 8B Schematic diagram for signalling element.

Figure 8C:
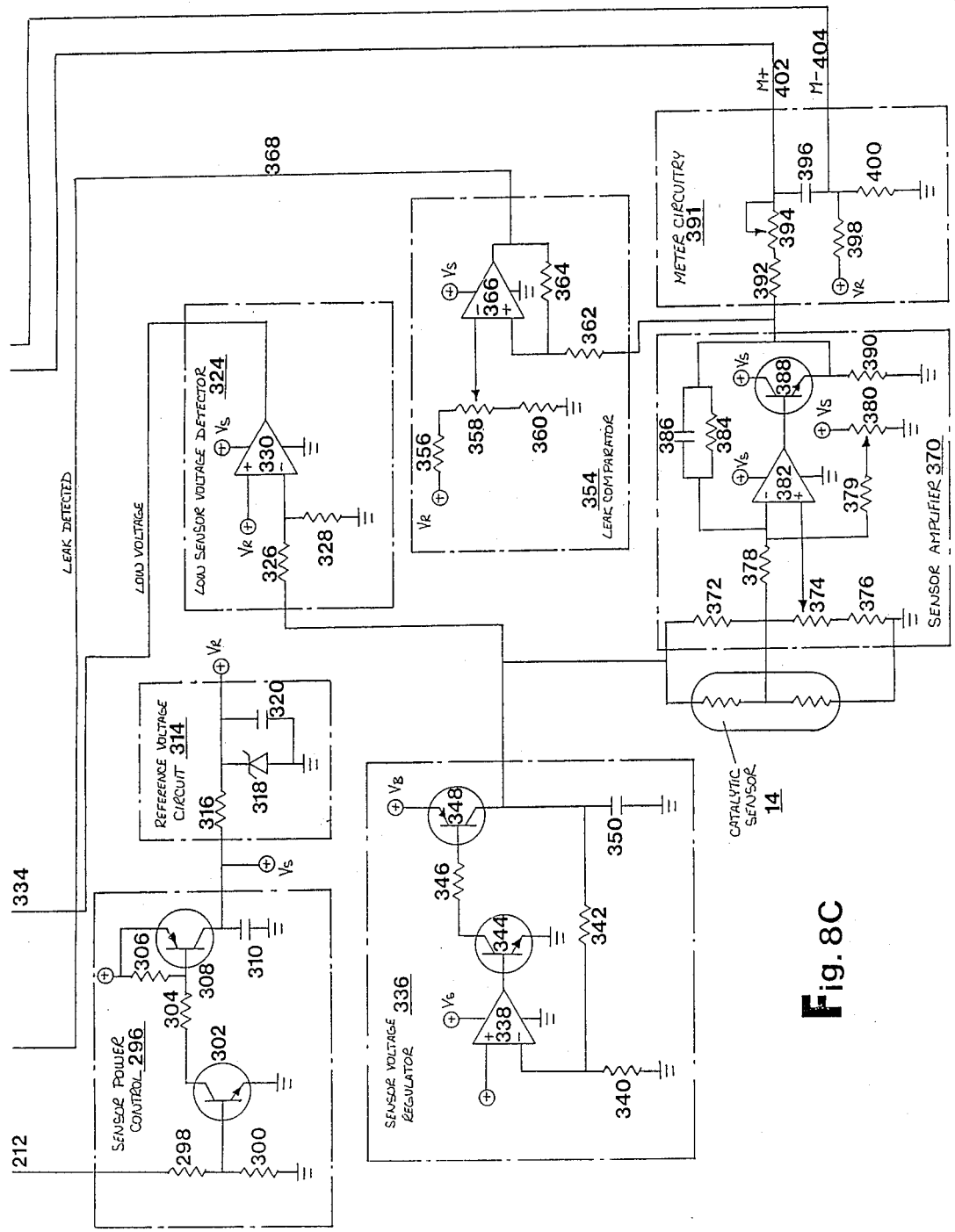

FIG. 8C Schematic diagram for sensing element.

Figure 9:
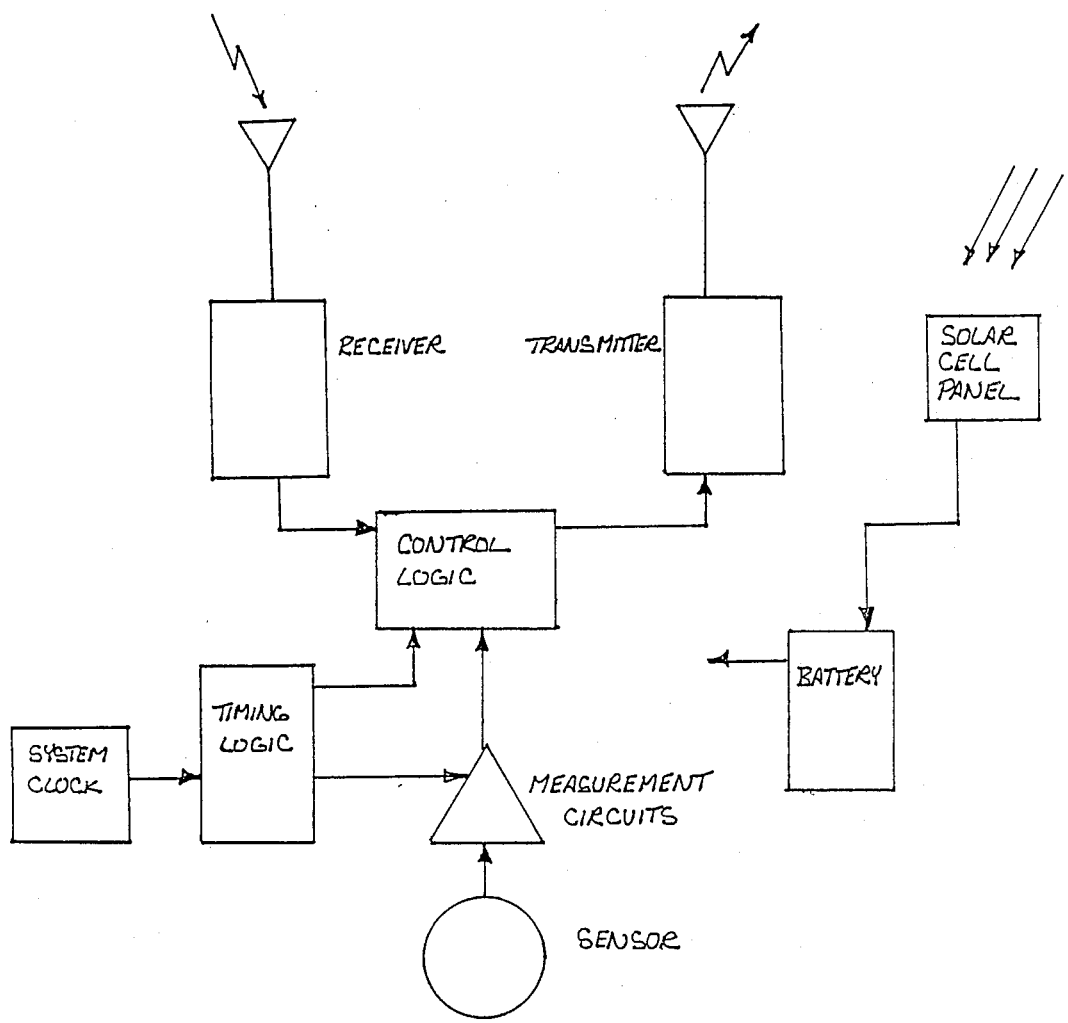

FIG. 9 Block diagram for radio communication and solar power.

Figure 10:
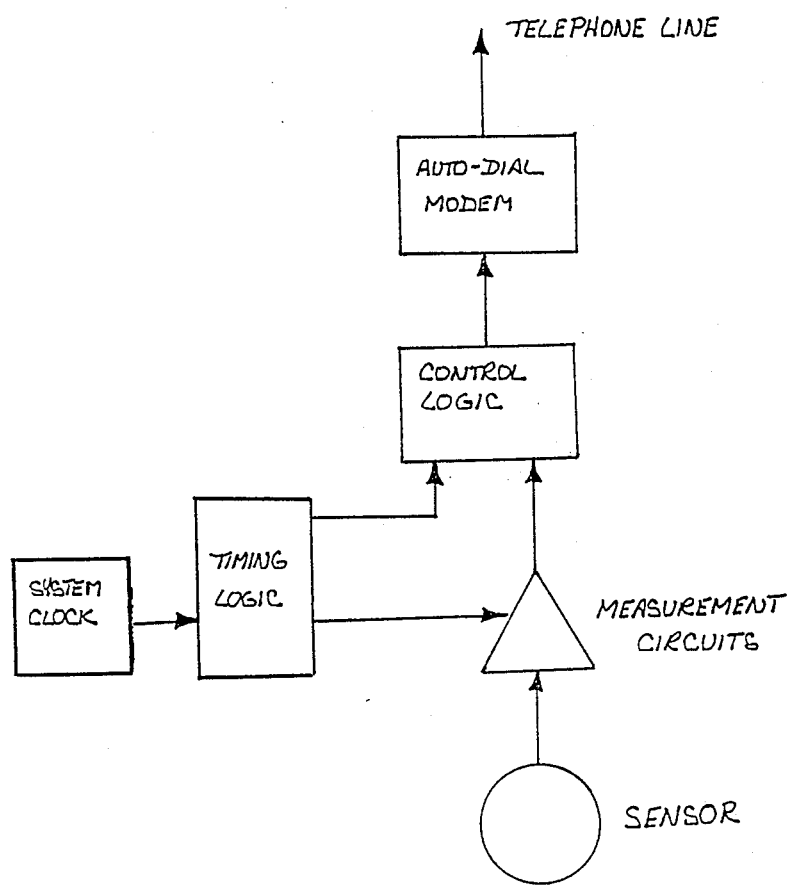

FIG. 10 Block diagram for telephone communication.

LIST OF DRAWING REFERENCE NUMERALS

10 Assembly Vapors Monitoring System
11 Pressure Contaminant Housing, Components 38 & 48
12 Sensor/Cable Housing
14 Gas Sensor
16 Machine screw
18 Sensor threaded assembly
20 Glass-Sealed Housing
22 Sub-Assembly Catalytic Sensor, Components 14, 18, & 20
24 Potting
26 Insulated Wiring
28 Phenolic Washer
30 Circuit Board Mounting Plate
32 Sub-Assembly Circuit Board & Components
34 Inner Tubular Housing
36 Windows 34, 180 deg. Apart for Circuit Board Assembly
38 Outer Threaded Tubular Pressure Housing
40 Sub-Assembly, Battery Contact Board
42 1.5 Volt "D" Cell
44 Protective Tape or Shrink Tubing
46 Battery Insertion Window in 34
47 Sub-Assembly Battery, Components Six Each 42
48 Sub-Assembly Catalytic Sensor, Electronics & Battery,
Components 12,16,22,24,26,28,30,32,34,40,42,56, 62 & 64
50 Battery Spring Contact
52 Cup Housing, Battery Spring Contact
54 Battery Contact Pin
56 Sub-Assembly Battery Spring Contact, Components 50,52 & 54
58 Concentric Contact Ring
60 Housing Concentric Contact Ring
62 Sub-Assembly Housing Concentric Contact Ring, Components 58 & 60
64 Spacer Ring
66 Spring Loaded Contact Housing
68 Spring Loaded Contact
70 Sub-Assembly Spring Contact Housing, Components 66 & 68
72 Glass-Sealed Pin & Bulk Head Housing
74 Compression Ring
76 Shear Load Washer
78 Electric Cable
80 Sub-Assembly Threaded Housing And Spring Contacts, Components 12,16,18,24,26,70,72,74 & 78
82 Instrument Protective Cap
84 Leak Indicator Lamp
86 Sensing Indicator Lamp
88 Test Bush Button
90 Leak Indicator Horn
92 Instrument Panel Housing
94 Instrument Cap Panel Spacer
96 Instrument Cap Body
98 Sound Emission Holes
100 Cable Termination Circuit Board
102 Cable Retention Housing
104 O-Ring
106 Conduit Cap Adapter
108 Rivet Band
110 Lock Ring Assembly
112 Instrument Head, Components 78,80,82, 84,86,88,90,92,94,96,100,102,104,106,108 & 110
114 Positive Meter Jack
116 Negative Meter Jack
118 Sub-Assembly Double Wall Underground Fuel Storage Tank (not part of the invention)
119 Freeze Line and Cool Line
120 Conduit to Surface ( not part of the invention)
122 Drain Pipe
124 Concrete ( not part of the invention )
126 Street Box ( not part of the invention )
128 Pad Lock ( not part of the invention )
130 Cover, Street Box ( not part of the invention )
132 Soil Strata Adjacent to Underground Tank part of the invention)
134 Ground Surface ( not part of the invention )
136 Holes Drilled In Cover, Sound Emission
138 Combustible Vapors ( not part of the invention )
165 Timing Element
166 System Clock Circuit
168 Resistor 170 Investor, Logic Gate
172 Resistor
174 Crystal
176 Capacitor
178 Capacitor
180 Twenty Four Hour Counter
182 Binary Counter, Twenty Eight Stage
184 Johnson Counter, Seven Stage
186 OR Logic Gate, Two Input
189 BLINK, Logic Signal
188 Timing Decode Logic
190 OR Logic Gate, Two Input
192 OR Logic Gate, Three Input
194 OR Logic Gate, Three Input
196 OR Logic Gate, Three Input
198 OR Logic Gate, Two Input
200 Invertor, Logic Gate
202 Resistor
204 Capacitor
206 Inverter, Logic Gate
208 D Flip-Flop
210 SAMPLE, Logic Signal
212 MEASURE, Logic Signal
214 FLASH, Logic Signal
216 TEST, Logic Signal
219 Power Element
220 Logic Power Control
222 Mercury Switch
224 Current Regulator Diode
226 Transistor
228 Flip-Flop
230 Capacitor
232 Capacitor
234 Resistor
235 Signalling Element
238 Alarm Latch
240 D Flip-Flop
242 Capacitor
244 Resistor
248 Non-Resettable Alarm Indicator
250 Resistor
251 Fuse
252 Transistor
256 Current Limiter
258 Resistor
260 Resistor
262 Resistor
264 RESET, Logic Signal
266 Alarm Driver
268 AND Logic Gate, Two Input
270 Resistor
272 Resistor
274 Transistor
276 Resistor
278 Resistor
282 Sensing Lamp Driver
284 NAND Logic Gate, Two Input
286 AND Logic Gate, Two Input
288 Resistor
290 Transistor
292 Resistor
294 Meter, Current
295 Sensing Element
296 Sensor Power Control
298 Resistor
300 Resistor
302 Transistor
304 Resistor
306 Resistor
308 Transistor
310 Capacitor
314 Reference Voltage Circuit
316 Resistor
318 Shunt Voltage Regulator
320 Capacitor
324 Low Sensor Voltage Detector
326 Resistor
328 Resistor
330 Voltage Comparator
334 LOW VOLTAGE, Logic Signal
336 Sensor Voltage Regulator
338 Operational Amplifier
340 Resistor
342 Resistor
344 Transistor
346 Resistor
348 Transistor
350 Capacitor
354 Leak Comparator
356 Resistor
358 Potentiometer
360 Resistor
362 Resistor
364 Resistor
366 Voltage Comparator
368 LEAK DETECTED, Logic Signal
370 Sensor Amplifier
372 Resistor
374 Potentiometer
376 Resistor
378 Resistor
379 Resistor
380 Potentiometer
382 Operational Amplifier
384 Resistor
386 Capacitor
388 Transistor
390 Resistor
391 Meter Circuitry
392 Resistor
394 Potentiometer
396 Capacitor
398 Resistor
400 Resistor
402 M+, Analog Signal
404 M−, Analog Signal

DESCRIPTION OF INVENTION

Referring to FIG. 1, the following is a description of the components of the mechanical assembly in our vapor monitoring system:

The assembly; vapors monitoring system 10, consists of an instrument sensor assembly 11 and instrument head assembly 112.

The sensor assembly 14 prior to final assembly is attached to 20 by compression glass and the assembly is soldered to 18 and thereby becomes 22.

The insulated wiring 26 is soldered to 22 as shown and held for later connection to 32.

The inner tubular housing 34 is assembled by bonding with 30,56 and 40 at locations as shown. Prior to assembly 56 is assembled by bonding from 50,52 & 54. Prior to assembly 40 is wired with 26. The prior assemblage is bonded to 22 using 24 and 28, wiring 26 is routed as shown. Sub-assembly 62 is assembled by bonding from 58 and 60. Wires 26 are soldered, attaching to 62 with lengths as required for routing to 36. Sub-assembly 62 is bonded to prior assembly as shown using 24. Sub-assembly 32 is installed as shown into the prior assembly. Wiring 26 is attached as required by soldering. The spacer ring 64 is bonded in place as shown. The prior assemblies thereby becomes the sub-assembly 48.

The spring contacts 68 are bonded into 66 and thereby becomes sub-assembly 70. The glass-sealed pin & bulkhead housing 72 is soldered to 18. The wires 26 are soldered to 70 and the assemblage of 18 & 72. The wires 26 are pre- cut to the required length as shown. The sub-assembly 70 is bonded into the assemblage 18 & 72 as shown. The electrical cable 18 is cut to desired length. The compression ring 74 is crimped into desired position. The assemblage of 74 & 78 is soldered to the appropriate pins of the assemblage housing 72. The shear load washer 76 and 12 are positioned as shown and secured by machine screws 16. The assemblage is potted with 24.

The opposite end of 78 is prepared and the assemblage of 102,104,106 & 108 is secured to 78 by crimping 74 in place as shown. The wires of 78 are prepared and soldered to 100 in the appropriate positions. The assemblage is potted by 24 as shown.

The Leak Indicator Horn 90 and 84,86 & 88 are assembled into the Instrument Panel Housing 92 as shown. Wires 26 are connected and the assemblage is potted with 24 as shown. The Instrument Cap Body 96 is assembled to 94 and the assemblage housing 92 by bonding. The wires 26 are soldered to the assemblage housing 100. The lock ring assembly 110 is assembled onto 96 as shown. The excess wire length of 26 is folded into the assemblage of housing 96 as 96 is bonded to the assemblage housing 102. Installation of removable instrument protective cap completes the sub-assembly 112.

The cells 42 are installed through the Battery Insertion Window 46, six cells become 47. The sub-assembly 48 is threaded into 38 and the assembly becomes 11. The subassembly 112 is threaded into 11 and becomes the system 10.

Referring to FIG. 2.

Removal of Instrument Protective Cap 82 exposes for viewing and function of 84,86,88,114 and 116. 84 a red lamp indicates leak detection. 86 a green lamp indicates active sensing. The Test Push Button 88 allows on demand sensing and resets the twenty four hour clock to the time of activation. The meter jacks 114 and 116 allow for plugging in a meter for vapor concentration determination in parts per million.

Referring to FIG. 3.

The catalytic sensor is shown at 14. The end of the sensor/cable housing is shown at 12. The sensor/cable housing 12 is held in place by machine screws 16 and are shown at 16.

Referring to FIG. 8.

The sensing element 295 is comprised of 296,314,324, 336,354,370 and 391. The timing element 165 is comprised of 166,180, and 188. The signalling element 235 is comprised of 112,238,248,256, 266 and 282.
The power unit 219 is comprised of 47 and 220.

Referring to FIG. 8A.

The System Clock Circuit 166 is comprised of an oscillator circuit formed by inverter logic gate 170, resistor 168, resistor 172, crystal 174, capacitor 176 and capacitor 178. The signal output from this circuit is responsible for all timing for the system. Crystal 174 is a low frequency tuning-fork type crystal calibrated for 18.641KHZ. This frequency was chosen because it can be divided evenly using binary counters to generate a count sequence which repeats every twenty four hours. Resistor 168, resistor 172, capacitor 178, and capacitor 176 provide the necessary biassing and phasing required for the inverter gate 170 to drive the crystal 174.

The Twenty Four Hour Counter 180 is formed by a twenty eight stage binary counter 182, which divides the clock signal by 268435456 to 1 ; with the chosen clock frequency the counter will repeat its' count cycle in four hours. The output of the binary counter 182 is fed to Johnson counter 184 which in conjunction with OR-gate 186 form a cycle counter for the binary counter 182. When the cycle count reaches six the cycle counter returns to zero and then starts counting cycles again. The return to zero denotes the completion of a twenty four hour period. It should be noted that when the Test push button 88, which activates the Reset logic signal 264, is depressed both counters are reset to start a twenty four hour counting cycle anew.

Blink logic signal 189 is the only signal output by the Twenty Four Hour Counter 180 which is not further processed by the Timing Decode Logic 188. It is used by the Sensing Lamp Driver 282 (FIG. 8B) to blink the Sense Indicator Lamp 86 to indicate a low battery condition. Blink logic signal 189 toggles at 2.28 hertz rate.

The Timing Decode Logic 188 provides a means to detect specific counts and ranges of counts output from the Twenty Four Hour Counter 180 and to generate from specific counts a variety of timing signals. Four timing logic signals are generated. They are referred to by name as: Measure 212, Sample 210, Flash 214 and Test 216.

Measure 212 is an active high (+V) signal which activates the measurement circuitry via the Sensor Power Control 296 circuitry (FIG.8C). As long as this signal is active the measurement circuitry is powered and operating. The period of this signal ( 1.875 minutes ) corresponds to the Twenty Four Hour Counter 180 range of 000000 Hex to 3FFFFF Hex. The range is decoded as follows: When the Binary counter 182 has completed six cycles the Johnson counter 184 output number six becomes high (+V) which is fed via OR-gate 186 to its' reset input, which immediately causes the zero output to become high (+V). The zero output is logically inverted by inverter 200 to a logic zero (0V). Since the binary counter 182 has just completed a count cycle all its outputs are logic zero (0V). With all the inputs to OR-gates 190, 192, 194 at logic zero (0V) the outputs of these gates are likewise zero (0V). OR-gate 196 receives as inputs the outputs of OR-gates 190, 192 and 194, with all its' inputs zero (0V) its' output is also zero (0V). The output of OR-gate 196 is fed to inverter 206 through the low pass filter network formed by resistor 202 and capacitor 204. The output of inverter 206 goes high (+V) which is the Measure 212 logic signal. The low pass filter prevents any glitches from the decoding logic due to propagation delays in the binary counter 182 from reaching the Sample 210 and Measure 212 outputs. Capacitor 204 is terminated to the positive voltage supply (VL) to prevent the false activation of either the Sample 210 or the Measure 212 signals during the system power-up. Measure 212 remains high until any one of its' inputs of OR-gates 190, 192 or 194 receive a high (+V) logic signal, the Q22 output of the binary counter 182 is the first to become high (+V) in the counting process following the counter value of 000000 Hex.

Following a reset, depressing the Test Push Button 88, the counters are set to zero (000000 Hex) starting Measure 212 at the beginning of its' interval, thus a measurement is taken for each depression of the Test Push Button 88.

(Hex refers to hexidecimal/number base 16 )

Sample 210 logic signal is zero (OV) during the measurement interval, while Measure 212 is active, but returns high (+V) just prior to Measure 212 deactivating. The return high , the raising edge, is used to latch the results of the current measurement into the Alarm Latch 238 (FIG. 8B).

Flash 214 logic signal is used by the Alarm Driver 266 circuitry to modulate the visual indicator (Leak Indicator Lamp 84) and the audio alarm (Leak Indicator Horn 90). This signal is best described as a 9 HZ signal gated on and off at 0.878 Second intervals.

Test 216 logic signal active high (+V) is used by the Alarm Driver 266 circuitry (FIG. 8B) to test the visual and audio alarm indicators following a system reset, initiated by depressing the Test Push Button 88. During the system reset D flip-flop 208 is cleared causing the Q-not output to become high (+V), which is the Test 216 logic signal. The Q-not output remains high (+V) until Q15 output of the Binary Counter 182 goes high (+V) clocking the logic value at the D input into the flip-flop. Test 216 will deactivate 0.878 Seconds from the time the Test Push Button 88 is released.

The Logic Power Control 220 circuit is responsible for turning the power on and off for the entire unit along with regulating the current draw of the time keeping logic circuits (System Clock 166, Twenty Four Hour Counter 180, and Timing Decode Logic 188).

The power is turned off by holding the unit with the Catalytic Sensor 14 end of the assembly 11 upwards, opening the mercury switch 222, which disconnects the battery 47 from all logic circuits including the Logic Power Control 220 circuit. If the assembly 11 is then held in its' normal operating position with the Catalytic Sensor 14 end down, closing the mercury switch 222, the Logic Power Control 220 circuit is reset during the power restoration putting the unit in a very low power sleep mode drawing in the order of 1 micro ampere or less. During power restoration capacitor 232 pulls the reset input of flip-flop 228 high (−V) causing the Q output to remain low (OV) preventing transistor 226 from conducting which disconnects voltage VL. Resistor 234 allows capacitor 232 to charge lowering the voltage at the reset input to logic zero (OV) in preparation for a system reset. When the Reset 264 logic signal is activated, by depressing the Test Push Button 88, flip-flop 228 is set causing the Q output to go high (+V) driving transistor 226 into conduction which connects voltage VL via current regulator diode 224 to the battery 47. The current regulator diode 224 limits the current delivered to the logic circuits to 220 micro amperes. Capacitor 230 provides filtering for voltage VL.

Refering to FIG. 8B.

At the end of a measurement period the result of the current measurement is latched into the Alarm Latch 238 to be held until the next measurement. The output of the Leak Comparator 354 (FIG.8C) circuit present through the low pass filter formed by resistor 244 and capacitor 242 to the D input is clocked into D flip-flop 240 by the rising edge of Sample 210 logic signal and is transfered to the Q output. The signal at the Q output is high (+V), indicating an alarm condition, if the results of the last measurement indicated a reading of combustible vapor concentration greater than the preset level. The low pass filter is required to prevent a false alarm condition being latched during system powerup. The output of the Alarm Latch 238 is connected to both the Non-Resettable Alarm Indicator 248 and the Alarm Driver 266.

In the Non-Resettable Alarm Indicator 248 circuitry the output of the Alarm Latch 238 is fed through resistor 250 driving transistor 252 into conduction which cause fuse 251 to burn open. With fuse 251 burned open it can be determined if an alarm condition occurred at some point in the units' operation since the last servicing, without relying on battery power or circuit function to maintain this indication.

In the Alarm Driver 266 circuitry the output of the Alarm Latch 238 is logically "ANDed" with Flash 214 logic signal by AND gate 268 to drive transistor 274 into conduction through resistor 270. Transistor 274 in turn drives the Leak Indicator Lamp 84 and the Leak Indicator Horn 90 through resistor 278 and resistor 276 respectively. When the Alarm Latch 238 output is high (+V) both alarm indicators are driven on and off at the rate set by the Flash 214 logic signal.

The Test 216 logic signal when activated (+V) also drives transistor 274 into conduction through resistor 272 causing the alarm indicators to turn on. This action allows for the testing of the Leak Indicator Horn 90 and Leak Indicator Lamp 84 without actually forcing the unit to sense a leak condition.

The Sensing Indicator Lamp 86 is driven by transistor 290 through resistor 292. Transistor 290 is in turn driven by the logical combination of the logic signals Measure 212, Blink 189, and Low Voltage 334 through resistor 288. The logical combination is preformed by NAND gate 284 which is connected to AND gate 286. During a measurement period the Sense Indicator Lamp 86 is driven on, but if proper voltage can not be maintained at the Catalytic Sensor 14 (FIG. 8C) the lamp will be driven on and then off at the rate of the Blink 189 signal.

The Current Limiter 256 limits the power that can be delivered, under any circuit fault conditions, to the Electrical Cable 78 and Instrument Head 112 assembly which are located outside the protective enclosure of the assembly 11 containing the sensor electronics. This limit on power provides the required intrinsic safety for both the Electric Cable 78 and the Instrument Head 112 which may be exposed to atmospheres loaded to explosive levels with combustible vapor. Resistor 258 limits the maximum current which can be delivered from the battery 47. Resistor 260 limits the current return from the Test Push Button 88, while resistor 262 pulls down the Reset 264 line to logic zero (OV) when the Test Push Button 88 is not depressed.

Resistors 278 and 276 of the Alarm Driver 266 and resistor 292 of the Sensing Lamp Driver 282 also provide power limiting.

Refering to FIG. 8C.

The Sensor Power Control 296 in response to Measure 212 logic signal turns on voltage VS which supplies power to the measurement circuitry. When Measure 212 logic signal is active (+V) transistor 302 is driven into conduction through resistor 298 which in turn drives transistor 308 through resistor 304, thus switching on voltage VS. Resistors 300 and 306 insure that transistors 302 and 308 respectively are both non-conducting when Measure 212 is low (OV). Capacitor 310 provides filtering for voltage VS.

The Voltage Reference Circuit 314 is responsible for maintaining a constant voltage reference VR of 2.5 volts during the entire battery life. Voltage VS powers a shunt regulater 318 through resistor 316 which sets the current consumed by the circuit. Capacitor 320 filters voltage VR. Voltage VR is used by the Sensor Voltage Regulator 336, Low Sensor Voltage Detector 324, Leak Comparator 354 and Sensor Amplifier 370.

The Sensor Voltage Regulator 336 circuit is the source of power for the Catalytic Sensor 14. The output voltage is set to 5 volts, which is constant over the battery life. Operational amplifier 338 drives transistor 344 which in turn drives transistor 348 until a voltage equal to the reference voltage VR connected to the "+" input is present at the "-" input. Resistors 340 and 342 set the amount of feedback and thereby set the output voltage. Resistor 346 limits the base drive to transistor 348. Capacitor 350 filters the output voltage. The Sensor Amplifier 370 also uses the 5 volt output to power the reference half of the bridge circuit.

The Sensor Amplifier 370 is a high gain DC (Direct Current) amplifier, which amplifies the difference between the SC, center tap, connection of the Catalytic Sensor 14 and the reference half of the bridge formed by resistors 372, 376 and potentiometer 374. With the Catalytic Sensor 14 in fresh air, no combustible vapor present, the inherent imbalance between the sensor and the circuitry can be compensated for by adjusting potentiometers 374 and 380. Due to the high gain of the amplifier the coarse zero adjustment is accompanied by potentiometer 374 and the fine adjustment by potentiometer 380. The value of resistors 372 and 376 set the sensitivity and range of the coarse zero adjustment capability resistor 379 does the same for the fine adjustment. The gain of the amplifier is set by resistors 378 and 384. The frequency response is set by capacitor 386, since the response of the Catalytic Sensor 14 is quite slow the amplifier response need not be much greater than 5 to 10 hertz. One of the reasons for limiting the response is to prevent any oscillations from developing in the measurement circuitry. Transistor 388 increases the current drive capability of the operational amplifier 382. Resistor 390 provides a return path to ground (OV) for transistor 388.

Also associated with the Sensor Amplifier 370 is the Meter Circuitry 391 which provides a means to read the actual output of the amplifier in parts per million (PPM) of combustible vapor detected. It receives input from the Sensor Amplifier 370 and outputs, appropriately scaled, a current proportional to the PPM sensed via lines M+402 and M−404. The calibration of the circuit is preformed by adjusting potentiometer 394 with the sensor in a 1000 PPM atmosphere for 1 milliampere reading at the meter 294 (FIG.8B). Capacitor 296 dampens the meter 294 response. Resistors 398 and 400 form a reference voltage between ground (OV) and VR (2.5 V) for the meter 294, since it is difficult to zero the Sensor Amplifier 370 near its' own power supply ground (OV).

The Leak Comparator 354 circuit is responsible for detecting outputs of the Sensor Amplifier 370 greater than a predetermined level set by potentiometer 358. The output of the circuit, Leak Detected 368 logic signal, is fed to the Alarm Latch 238 (FIG.8B) which latches the output at the conclusion of the measurement period. Hysteresis in the comparator circuit is generated by resistors 362 and 364, which prevents indecisiveness of the comparator 366 when the Sensor Amplifiers 370 output is at or near the predetermined threshold. Resistors 356 and 360 set the sensitivity and range of adjustment of the level set by potentiometer 358.

The Low Sensor Voltage Detector 324 circuit monitors the Sensor Voltage Regulators 336 output and compares it against VR, the 2.5 V reference, with appropriate scaling. If The regulator output drops below a predetermined level the circuit will indicate the low voltage condition by activating the Low Voltage 334 logic signal (+V). Resistors 320 and 328 scale the Sensor Regulator 336 output voltage for comparison with VR by comparator 330.

OPERATION OF INVENTION

Referring to FIG. 4.

The assembly Vapors Monitoring System 10 is shown in a typical installation whereas 10 is monitoring BTX vapors 138 channeled by conduit 120 from a fuel leak in a double wall underground fuel storage tank 118. The electrical cable 78 suspends the sensor assembly 11 to its' optimum position and provides electrical power to 112. The assembly of 38, 48 and threaded end of 112 houses the electrical components in a pressure vessel and thereby complies with Underwriters Laboratories (U.L.) regulations for intrinsically safe. The catalytic sensor 14 is listed with U.L for intrinsically safe. Current supplied to 112 via 78 is amperage limited and thereby complies with U.L. intrinsically safe regulations.

The Instrument Head 112 is positioned at the top of the conduit 120. The Conduit Cap Adapter 106 is bonded to 120 and 102 inserts into 96 and the joint is sealed by the O-ring 104. Pad Lock 128 prevents theft of 10. At ground level 112 is protected by a Street Box 126 held in position by concrete 124. The cover 130 is modified by holes 136 see FIG. 6. The drain pipe 122 drains water from the cavity of 126. Bonding and O-ring seal prevents water entrance into 120.

Referring to FIG. 5.

The soil strata adjacent to underground tank 132 is monitored by 10 via 120. The vapors 138 from an uncontrolled leak migrate through strata and enter the conduit 120 through perforations.

The balance of the systems function and assembly for 11, 112, 122, 124, 126, 128 & 130 duplicates FIG. 4.

Referring to FIG. 6.

The cover, Street Box 126 is modified by sound emission holes 136 drilled in the cover.

Refering to FIG. 7.

The following is a description of the elements of the circuitry contained in our vapor monitoring system:

The Battery 47 is the source of power for the entire system. Its' output voltage is denoted by VB.

The Logic Power Control 220, powered by VB, switches the voltage VL to the system logic. The voltage VL is switched on when the Reset 264 logic signal is activated and is switched off when the position sensing means, mercury switch 222, contained in the Logic Power Control 220 detects a specific orientation of the Instrument Sensor Assembly 11.

The System Clock 166, powered by VL, is a crystal controlled oscillator which provides the time reference for the Twenty Four Hour Counter 180. When VL is switched on the System Clock 166 becomes active.

The Twenty Four Hour Counter 180, powered by VL, counts the System Clock 166 and repeats its' count sequence in one twenty four hour period. Selected taps are output to the Timing Decode Logic 188. When the Reset 264 logic signal is activated the counter is set to zero count (all outputs equal to logic zero OV). The Blink 189 logic signal is a toggling output which is used by the Sensing Lamp Driver 282 to time the lamp blinking rate.

The Timing Decode Logic 188, powered by VL, decodes the aforementioned selected tap outputs of the Twenty Four Hour Counter 180 into specific time periods during the twenty four hour count sequence. The decoded output Measure 212 logic signal when active causes the system measurement period to occur. The Sample 210 logic signal output signals the end of the measurement period and to latch the results of the current measurement. The Flash 214 logic signal is a toggling signal used to modulate the Leak Indicator Lamp 84 and the Leak Indicator Horn 90. The Test 216 logic signal causes the test period for the Leak Indicator Lamp 84 and Leak Indicator Horn 90, which was initiated by the activation of the Reset 264 logic signal.

The Sensor Power Control 296 switches the sensor voltage VS on and off in response to the Measure 212 logic signal. It receives its' power directly from the battery voltage VB and outputs VS to activate the measurement circuitry.

The Reference Voltage Circuit 314, powered by VS, creates the reference voltage VR which is used by other circuits and is unaffected with voltage changes occurring in the battery voltage VB during the usefull life of the battery 47.

The Sensor Voltage Regulator 336, powered by VB, regulates the voltage supplied to the Catalytic Sensor 14 and the bridge elements contained in the Sensor Amplifier 370.

The Low Sensor Voltage Detector 324, powered by VS, compares the Sensor Voltage Regulator 336 output voltage appropriately scaled with the reference voltage VR. If the sensor voltage is detected lower then a preset level then the Low Voltage 334 logic signal output is activated.

The Catalytic Sensor 14 is the means by which combustible vapors are detected in the measured atmosphere. It fundamentally consists of two resistive heating elements with one element coated with a platinum compound and the other coated with a similar but non-platinum compound. The platinum coated element is sensitive to the combustible vapors in the atmosphere owing to the catalytic combustion of said vapors when heated, thus causing greater heating and thereby increasing its' electrical resistance in relation to the non-platinum coated element. Since the platinum and non-platinum elements are wired in series and supplied by a constant voltage the voltage at the junction between the elements will shift in relation to each end of the network when in the presents of a combustible atmosphere. The voltage at the junction, the sensor output, is presented to the Sensor Amplifier 370 which amplifies the difference in voltage between a non-combustible atmosphere and a combustible atmosphere.

The Sensor Amplifier 370, powered by VS, amplifies the sensor output by a fixed gain before it is output to the Leak Comparator 354 and to the Meter circuitry 391.

The Meter circuitry 391 converts the Sensor Amplifier 370 output to a current proportional to the parts per million (PPM) of the combustible vapor in the atmosphere being sensed and then delivers said current to the Meter 294 over signal lines M+402 and M−404 via the Instrument Head Assembly 112.

The Leak Comparator 354, powered by VS, compares the current output of the Sensor Amplifier 370 with a predetermined voltage level which represents an atmosphere with a known percentage of combustible vapor. The voltage level is scaled from VR reference voltage and is therefore constant during the life of the battery 47. If the Sensor Amplifier 370 output is greater than the said voltage level Leak Detected 368 logic signal is activated.

The Alarm Latch 238, powered by VL, is triggered by the Sample 210 logic signal and once triggered will retain at its' output the results of the last measurement period as presented by the Leak Detected 368 logic signal.

The Non-resettable Alarm Indicator 248, powered by VB, is activated by the output of the Alarm Latch 238. When activated a non-resettable indicator means is set to indicate that an alarm has occurred since the last equipment servicing. In our embodiment the non-resettable indicator means is accomplished by a fuse 251 which is burned open upon an alarm.

The Alarm Driver 266, powered by VL, drives both the visual alarm indicator (Leak Indicator Lamp 84) and the audio alarm (Leak Indicator Horn 90), both contained in the Instrument Head Assembly 112. Activated by the output of the Alarm Latch 238 the Alarm Driver 266 drives the alarm indicators in a pulsing manner by logically combining the Flash 214 logic signal within the driver circuitry. The Test 216 logic signal when active forces the driver on causing both the Leak Indicator Lamp 84 and Leak Indicator Horn 90 on, thus allowing indicator testing without an alarm condition.

The Sense Lamp Driver 282, powered by VL, drives the Sensing Indicator Lamp 86 during the measurement period. If during the measurement period the Low Voltage 334 logic signal becomes active, then the Sensing Indicator Lamp 86 will be driven in a pulsing manner by logically combining the Blink 89 logic signal within the drive circuitry, which causes the lamp to blink indicating a low battery condition.

The Current Limiter Circuits 256 are required to limit the total current available to the Electrical Cable 78 and the Instrument Head Assembly 112 for the purposes of intrinsic safety of the unprotected components exposed to potentially combustible atmospheres.

CONCLUSION AND SCOPE

Federal and state laws have mandated the requirement for determining in a timely fashion the possible leakage of all underground fuel storage tanks. The immediate replacement of all existing tanks is not economically feasible. Filling the tanks with fuel to leak test is costly and the test does not yield the accuracy required. Drilling shallow monitor wells adjacent to existing tanks is feasible providing no other disturbance to surface paving is required. The self contained battery operated system disclosed herein provides the system required, by using the earths uniform temperature range summer to winter, thusly making battery power possible. Additionally sensors are utilized that allow long periods of off time and short operating intervals and are able to sense accurately, this combination extends battery life from hours to years. Thusly the invention delineated herein removes the requirement for remote control of the downhole sensor and thereby no costly installation of underground power and communication lines are required.

By reducing the task to the installation of a shallow depth monitor well adjacent to the underground fuel storage tank, and installing therein a completely self contained vapors monitoring system the task is greatly simplified and thereby made feasible. The system eliminates the requirement for skilled technicians for installation. The system by operating underground, below the freezeline, removes the effect of temperature changes on battery power and sensor low cost, makes feasible the implementation of the law. The system by its' small size and standalone features enhances possible application, for its' use. An example of extended use is the monitoring of existing water wells for fuel and other contamination. The primary risk from leaking underground fuel storage tanks is the contamination of domestic drinking water. With the inventions small size, low cost and standalone features, existing water wells can be monitored without delay and high cost.

Further, owning to the ability of the invention to standalone it can be easily extended to applications where a vapor detection system is required to operate for long periods of time at remote locations, such as along cross-country pipelines, by simply changing the type of signaling means employed. FIGS. 9 and 10 show two types of signaling alternatives.

FIG. 9 illustrates a system configuration utilizing radio frequencies for communication. In this configuration vapor is sensed for at timed intervals and the results stored in the Control Logic. In order to conserve battery power the transmission of the measurement results is done in response to an interrogation signal. During the intervals between high power demands, such as vapor sensing or transmissions, the battery is recharged by a solar cell panel.

FIG. 10 illustrates a system configuration utilizing an Auto Dial Modem to signal the detection of vapor over telephone lines. In this configuration the vapor is likewise sensed for at timed intervals, but if vapor is detected above a set limit the Control Logic instructs the modem to dial a give number and signal to the answering equipment that vapor has been detected.

We claim:

1. Apparatus for detecting hazardous gases comprising:
    a pressure containment housing adapted to be placed in a well or conduit to a predetermined depth below ground level;
    an instrument head;
    an electrical cable coupling the instrument head to the pressure containment housing, said cable having a length sufficient to allow the instrument head to be located near the top of the well or conduit when the pressure containment housing is in the well or conduit at said predetermined depth below ground level;
    an actuatable signalling means within the instrument head;
    a gas sensor carried by the housing for sensing the presence of hazardous gases in the well or conduit at said predetermined depth below ground level;
    a portable power unit carried by the housing and coupled with the gas sensor and the signalling element by way of said electrical cable to actuate the signalling means when power is supplied by the power unit to the gas sensor; and
    timing means carried by the housing and coupled with the power unit to supply electrical power to the gas sensor and the signalling means periodically.

2. Apparatus as set forth in claim 1, wherein the instrument head, the cable and the housing are not physically connected to structure externally of the housing, the cable and the instrument head.

3. Apparatus as set forth in claim 1, wherein said sensor comprises a catalytic sensor.

4. Apparatus as set forth in claim 1, wherein the signalling means includes means for indicating the presence of hazardous gases in the region of the well or conduit adjacent to the housing with said indicating means being capable of operating without being resettable.

5. Apparatus as set forth in claim 4, wherein said housing, said gas sensor, said power unit, said timing means, said cable, said instrument head and said signalling means define a self-contained unit out of engagement with the well or conduit when the housing is in the well.

6. Apparatus as set forth in claim 1, wherein said signalling means is a device for emitting coded lights.

7. Apparatus as set forth in claim 1, wherein said signalling means is a device for emitting coded acoustic waves.

8. Apparatus as set forth in claim 1, wherein said signalling means is a device for emitting coded radio frequency signals.

9. Apparatus as set forth in claim 1, wherein said signalling means is a modem for transmitting coded telephonic signals.

10. Apparatus as set forth in claim 1, wherein said sensor includes a device calibrated for detection of benzene, toluene and xylene gases.

11. Apparatus as set forth in claim 1, wherein said power unit includes a plurality of electrical storage devices.

12. Apparatus as set forth in claim 1, wherein said power unit includes a battery.

13. Apparatus as set forth in claim 1, wherein said power unit is a rechargeable battery.

14. Apparatus as set forth in claim 1, wherein said power unit is a rechargeable battery with a solar recharging element.

15. Apparatus as set forth in claim 1, wherein said signalling means operates at a voltage and current below levels required for igniting combustible gases.

16. Apparatus as set forth in claim 1, wherein said predetermined depth is a depth below the upper level of a constant temperature region below ground level.

17. Apparatus as set forth in claim 1, wherein said cable comprises a plurality of electrical conductors extending between the sensor and the signalling means.

18. Apparatus as set forth in claim 1, wherein said timing means provides an output signal which is cyclic.

19. Apparatus as set forth in claim 1, wherein the gas sensor is responsive to combustible gases in a relatively short time interval.

* * * * *